(12) United States Patent
Factor

(10) Patent No.: US 6,350,444 B1
(45) Date of Patent: Feb. 26, 2002

(54) GENE THERAPY FOR PULMONARY EDEMA USING ADENOVIRUS VECTORS ENCODING NA,K-ATPASE

(75) Inventor: Philip H. Factor, Glencoe, IL (US)

(73) Assignee: Edema Clearance, Inc., Glencoe, IL (US)

(*) Notice: Subject to any disclaimer, the term of this patent is extended or adjusted under 35 U.S.C. 154(b) by 0 days.

(21) Appl. No.: 09/470,007

(22) Filed: Dec. 22, 1999

Related U.S. Application Data

(60) Provisional application No. 60/114,721, filed on Dec. 28, 1998.

(51) Int. Cl.[7] .............................................. A61K 48/00
(52) U.S. Cl. ...................... 424/93.2; 514/44; 435/320.1
(58) Field of Search ........................ 536/23.5; 435/69.1, 435/320.1, 328; 514/44; 424/93.2

(56) References Cited

U.S. PATENT DOCUMENTS

| | | | |
|---|---|---|---|
| 5,698,202 A | 12/1997 | Ertl et al. ................. | 424/199.1 |
| 5,747,072 A | 5/1998 | Davidson et al. ........... | 424/93.2 |
| 5,792,453 A | 8/1998 | Hammond et al. ....... | 424/93.21 |
| 6,013,638 A * | 1/2000 | Crystal et al. ................. | 514/44 |

OTHER PUBLICATIONS

Crystal R., "Transfer of Genes to Humans: Early Lessons and Obstacles to Success." Science, vol. 270: 404–410, Oct. 1995.*

Deonarain, M., "Ligand–targeted receptor–mediated vectors for gene delivery." Exp. Opin. Ther. Patents, vol. 8 (1): 53–59, 1998.*

Miller et al., "Targeted vectors for gene therapy." FASEB, vol. 9: 190–199, Feb. 1995.*

Verma et al., "Gene therapy—promises, problems and prospects." Nature, vol. 389: 239–242, Sep. 1997.*

Orkin et al., "Report and recommendations of the panel to assess the NIH investment in research on gene therapy." pp. 1–20, Dec. 1995.*

Factor, P. et al. (1995) "Effects of Adenoviral Mediated Transfer of Na, K–ATPase Subunit Genes to Alveolar Epithelial Cells" *Annal NY Acad Sci* 834: 104–107.

Factor, P. et al. (1996) "Overexpression of the Na, K–ATPase, $\alpha_1$ Subunit Increases Na, K–ATPase Function in A549 Cells" *Am J Resp Crit Care Med* 153:A509.

Factor, P. et al. (1997) "Differential Effects of Adenoviral–Mediated Transfer of Na+/K+–ATPase Subunit Genes in Lung Epithelial Cells" *Chest* 111: 110S–111S.

Factor, P. et al. (1998) "Overexpression of the Na, K–ATPase $\alpha_1$ Subunit Increases Na, K–ATPase Function in A549 Cells" *Am J Respir Cell Mol Biol* 18: 741–749.

Factor, P. et al. (1998) "Augmentation of Lung Liquid Clearance via Adenovirus–mediated Transfer of a Na, K–ATPase $\beta_1$ Subunit Gene" *J Clin Invest* 102(7): 1421–1430.

Factor, P. et al. (1999) "Adenoviral–Mediated Overexpression of the Na, K–ATPase $\beta_1$ Subunit Gene Increases Lung Edema Clearance and Improves Survival During Acute Hyperoxic Lung Injury in Rats" 2nd Annual Meeting, American Society of Gene Therapy Washington, DC.

Factor, P. et al. (1999) "Adenoviral–Mediated Overexpression of the Na, K–ATPase $\beta_1$ Subunit Gene Increases Lung Edema Clearance and Improves Survival During Acute Hyperoxic Lung Injury in Rats" *Chest* 116: 24S–25S.

Factor, P. et al. (1999) "Adenoviral–Mediated Overexpression of a Na, K–ATPase β Subunit Gene Improves Lung Edema Clearance in Rats with Hydrostatic Pulmonary Edema" *Am J Respir Crit Care Med* 159: A216.

Factor, P. et al. (1998) "Augmentation of lung liquid clearance via adenovirus–mediated transfer of Na, K–ATPase beta1 subunit gene," *J. Clin. Invest.* 102(7): 1421–1430.

Factor, P. et al. (1998) "Overexpression of the Na+, K+–ATPase alpha1 subunit increase Na+, K+–ATPase function in A549 cells," *American Journal of Respiratory Cell and Molecular Biology*. 18(6): 741–749.

Morsy M. A. et al. (1998) "An adenoviral vector deleted for all viral coding sequences results in enhanced safety and extended expression of a leptin transgene," Proceedings of the National Academy of Sciences of the United States of America 95: 7866–7871.

Mitani K. et al. (1995) "Rescue, propogation, and partial purification of a helper virus–dependent adenovirus vector," Proceedings of the National Academy of Sciences of the United States of America, U.S., National Academy of Science 92:3854–3858.

Schiedner. G. et al. (1998) "Genomic DNA transfer with a high–capacity adenovirus vector results in improved in vivo gene expression and decreased toxicity," *Nature Genetics* 18:180–183).

Amalfitano A. et al. (1998) "Production and characterization of improved adenovirus vectors with the E1, E2b, E3 genes deleted," *Journal of Virology* 72: 926–933.

* cited by examiner

*Primary Examiner*—Dave T. Nguyen
(74) *Attorney, Agent, or Firm*—Alex O. Martin; Barnes & Thornburg

(57) ABSTRACT

Methods and compositions are provided for gene therapy for pulmonary edema in mammals by the transfer of Na,K-ATPase subunit genes to lung epithelial cells for the purpose of increasing levels of Na,K-ATPase in vivo. Recombinant adenoviral vectors mediate the transfer of the Na,K-ATPase subunit genes into lung epithelial cells. The vectors employ expression control sequences consisting of viral derived promoter elements linked to cDNAs that express Na,K-ATPase subunit genes. These genes have been shown to be capable of generating the transepithelial osmotic gradient responsible for the movement of water across epithelial membranes thereby causing pulmonary edema clearance in mammalian lungs.

7 Claims, 10 Drawing Sheets

Dorsal  Ventral

GENE THERAPY FOR PULMONARY EDEMA USING ADENOVIRUS VECTORS ENCODING NA,K-ATPASE

This application claims priority from co-pending U.S. provisional application 60/114,721 filed Dec. 28, 1998.

BACKGROUND OF THE INVENTION

Methods and compositions are provided for gene therapy for pulmonary edema by the transfer of Na,K-ATPase subunit genes to lung epithelial cells for the purpose of increasing levels of Na, K-ATPase in vivo.

Cardiogenic and non-cardiogenic pulmonary edema affect millions of people each year causing substantial morbidity and mortality (Large State Peer Review, 1997). The alveoli of these people flood with liquid from pulmonary capillaries which compromises oxygen transfer to the systemic circulation (Hall et al., 1986). This sequence of events results in hypoxemia, hypercapnia, and death if no corrective measures are taken.

Unfortunately, no specific or satisfactorily effective treatment for pulmonary edema is available. Current therapy is entirely supportive and includes diuretic therapy to reduce pulmonary capillary hydrostatic pressure. This therapy has been shown to reduce edema accumulation but does not influence pulmonary edema clearance (Sznajder et al., 1986). In many cases, this therapy leads to inappropriately low left ventricular end diastolic volumes, reduced cardiac output, hypotension, and decreased peripheral oxygen delivery. Therapies that would improve or reconstitute the lung's ability to keep itself dry could reduce the morbidity associated with pulmonary edema. (Matthay, et al., 1990, Verghese, et al., 1999)

Edema accumulates in the alveolus of the lung as a result of increases in capillary permeability and/or hydrostatic pressure, as described by Starling's equation. (Staub, 1980) Conversely, edema is cleared from the alveolus as a result of active transport of $Na^+$ out from the alveolar air space. This $Na^+$ transport is due to the action of Na,K-ATPases that are located on the basolateral surface of alveolar type 2 epithelial (AT2) cells. These ATPases generate a transepithelial osmotic gradient that causes fluid movement out of the alveolar airspace via trans- and para- cellular pathways.

Lung edema clearance resulting from active $Na_+$ transport has been demonstrated in live animal models, in isolated rat lungs, and in humans (Matthay and Wiener-Kronish, 1990; Effors et al., 1989; and Goodman et al., 1983). Supporting the role of active $Na^+$ transport in lung liquid clearance are experiments in isolated rat lungs which demonstrate that lung liquid clearance is completely stopped by hypothermia (via inhibition of active transport), and is decreased by both amiloride (a $Na^+$ channel inhibitor) and ouabain (a Na,K-ATPase inhibitor).

Na,K-ATPases are expressed in all eukaryotic cells where they are essential for the maintenance of cell volume and intracellular pH. They are also important for vectorial ion movement in many transporting and secretory epithelial throughout the human body. In particular, these ATPases are expressed in the alveolar epithelium where they reside on the basolateral aspect of alveolar type 2 cells.

Na,K-ATPase molecules are well controlled heterodimers. Endogenous Na,K-ATPase expression on the cell surface is tightly regulated and depends on changes in either intracellular $Na^+$ or cell volume. As the stimulus for increased Na,K-ATPase activity abates, it is phosphorylated via protein kinase A (PKA) and/or protein kinase C (PKC) leading to internalization into late endosomes, creating cytoplasmic stores of assembled, potentially functional Na,K-ATPases. If needed, these Na,K-ATPase containing vesicles can be rapidly recruited to the cell membrane to meet immediate needs, should $Na^+$ concentration or cellular volume change. In addition, intracellular pools of unassembled Na,K-ATPase subunit proteins exist in subcellular organelles and are also available for rapid assembly and recruitment to the cell membrane. Results of work by others suggest that there should be no need for additional, exogenous Na,K-ATPases.

Na,K-ATPases utilize high energy phosphates to exchange intracellular $Na^+$ for extracellular $K^+$. In addition to effecting vectorial $Na^+$ movement, Na,K-ATPases regulate cell volume and intracellular pH and are responsible for transmembrane potentials in depolarizable cells. Functional Na,K-ATPase is composed of two subunits, ($\alpha$ and $\beta$. Both subunits are required for normal Na,K-ATPase function. Three isoforms of each subunit have been identified and cloned. The $\alpha$ subunit has ATPase activity and is responsible for $Na^+/K^+$ exchange. The $\beta$ subunit controls heterodimer assembly and life span, and trafficking to the plasma membrane. Although all cells express these proteins, isoform expression (e.g. $\alpha_1/\beta_1$, $\alpha_1/\beta_2, \alpha_2/\beta_1$) is developmentally regulated and differs between tissues. The $\alpha_1$, $\alpha_2$, and $\beta_1$ subunits are the principal subunits expressed in rat lung.

Lungs of rats exposed to subacute hyperoxia (85% of $O_2 \times 7$ days) have increased lung edema clearance (Olivera et al., 1994). These findings were associated with increased AT2 cell and whole lung Na,K-ATPase expression. Rats exposed to acute hyperoxia (100% of $O_2 \times 64$ hours) have decreased Na,K-ATPase expression and decreased lung liquid clearance. Thus, Na,K-ATPase expression and function parallel lung liquid clearance following hyperoxic lung injury.

Recombinant genetic technology has not been applied to treat lung injury. A possible approach is to use replication deficient adenoviruses which are useful for gene transfer. Adenoviruses are tropic for the respiratory epithelium, infect non-replicating cells with high efficiency, and do not integrate into the host genome. The absence of a crucial gene ($E_{1a}$) makes it impossible for adenoviruses to replicate outside of cells that express $E_{1a}$. Hence, adenoviruses do not propagate following infection of eukaryotic cells that do not express $E_{1a}$. These recombinant vectors can be constructed with powerful promoters that allow high level, transient expression of a gene of interest in a cell transduced by adenoviruses.

A problem with the use of adenoviruses to transfer genes for therapy is that early ($1^{st}$ and $2^{nd}$) generation adenoviruses have been reported to cause significant host responses that limit their use for human gene therapy. These inflammatory effects are due, in part, to the expression of adenoviral antigens on the cell surface of transduced cells. These antigens cause a cytotoxic T-cell response that leads to elimination of the transduced cells. Suitable vectors for the delivery and short-term expression of many genes in the lung may be high-capacity, helper-virus dependent adenoviruses that contain no genes that express adenoviral proteins. Consequently it is expected that much of the anti-adenovirus host response will be abrogated by the use of these vectors, as such they are excellent. These vectors are also capable of gene transfer to cells in vitro. As such, these vectors are useful for the production of recombinant protein.

A goal is to use adenoviruses to develop gene therapy for lung illnesses, including pulmonary edema. Currently available treatments for pulmonary edema are unable to affect the lung's ability to remove excess fluid from the alveolar airspace without affecting other organs. Thus, no specific treatments for pulmonary edema are currently available. The development of treatments that specifically affect pulmonary edema require the delivery of complex, functional proteins to alveolar epithelial cells. Currently there exists no pharmaceutical delivery system, other than gene transfer, that is capable of highly efficient overexpression of transport proteins such Na,K-ATPase in the alveolar epithelium.

Replication deficient adenoviruses have been previously used for human gene transfer studies. Most of these are phase I studies that have focused on the treatment of heritable conditions and cancer, and have yielded limited results. Gene therapy has not been reported for the treatment of acute or life threatening conditions. The use of these vectors for acquired conditions such as pulmonary edema would represent a new use for these vectors.

SUMMARY OF THE INVENTION

The invention relates methods and compositions for reducing pulmonary edema in acquired diseases of the mammalian lung using recombinant genetic technology. Adenoviruses are preferred vectors for the treatment of acquired, acute/short-term illnesses of the lung. A method of the invention includes the following steps:
  (a) obtaining a recombinant genetic vector including
    (i) an adenovirus that has no nucleotide sequences encoding adenovirus proteins; and
    (ii) nucleotide sequences encoding Na,K-ATPase subunit genes that encode at levels that are an overexpression compared to levels in lung cells not having the genetic vector, and
  (b) transferring the genetic vector into epithelial cells of the lung in vivo under conditions that allow expression of the subunit genes.

The invention also relates a recombinant genetic vector including:
  (a) an adenovirus that has no nucleotide sequences encoding adenovirus proteins; and
  (b) nucleotide sequences encoding Na,K-ATPase subunits at levels that are an overexpression compared to levels in lung cells not having the genetic vector.

An aspect of the invention is a host cell into which a recombinant genetic vector has been transferred, said vector including:
  (a) an adenovirus that has no nucleotide sequences encoding adenovirus proteins; and
  (b) nucleotide sequences encoding Na,K-ATPase subunits at levels that are an overexpression in vivo compared to levels in lung cells not having the genetic vector.

Suitable host cells include epithelial cells, in particular lung epithelial cells. Expression of genes from the vector in the host cell could take place in vitro or in vivo but the latter is preferred for clinical use. The present invention provides methods and compositions for the transfer of Na,K-ATPase subunit genes to lung epithelial cells and expression of the genes for the purpose of increasing in vivo Na,K-ATPase activity and improving lung liquid clearance. These methods and compositions are designed to augment endogenous alveolar transport processes for the purposes of gene therapy for pulmonary edema. Experimental data indicates that augmentation of Na,K-ATPase activity in vitro and in vivo requires overexpression of only one subunit (Factor, et al., 1998 a and b). The rate limiting( subunit varies among cell types, organs, and species. Selection of one of the three possible subunits is preferred and will vary between species and cell type. The use of a single subunit is desirable because it simplifies adenovirus construction and propagation, allows optimization of adenovirus design and minimizes cellular metabolic responses required to synthesize more than one transgene. For example, adenoviral-mediated gene transfer and expression of a ,$\beta_1$ or $\alpha_2$ subunit gene increases Na,K-ATPase activity in rat cells and increases lung liquid clearance in rat lungs, whereas transfer of an $\alpha_1$ subunit gene is required to affect changes in active $Na^+$ transport in human lung cells or monkey lungs.

DETAILED DESCRIPTION OF THE INVENTION

Figure 1:
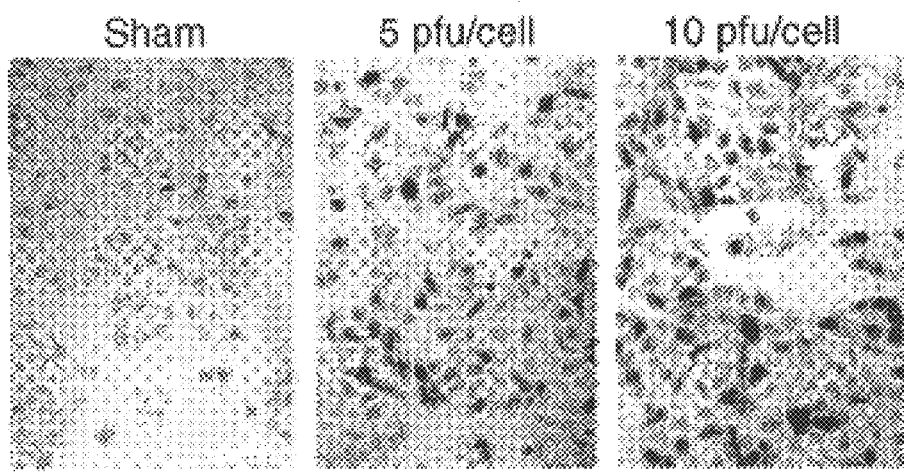
FIG. 1 is a photomicrograph that shows rat AT2 cells infected with 0 (sham), 5, or 10 pfu/cell of the vector ad$\beta$-gal; X-gal staining for gene expression was performed 48 hours after infection.
Figure 2:
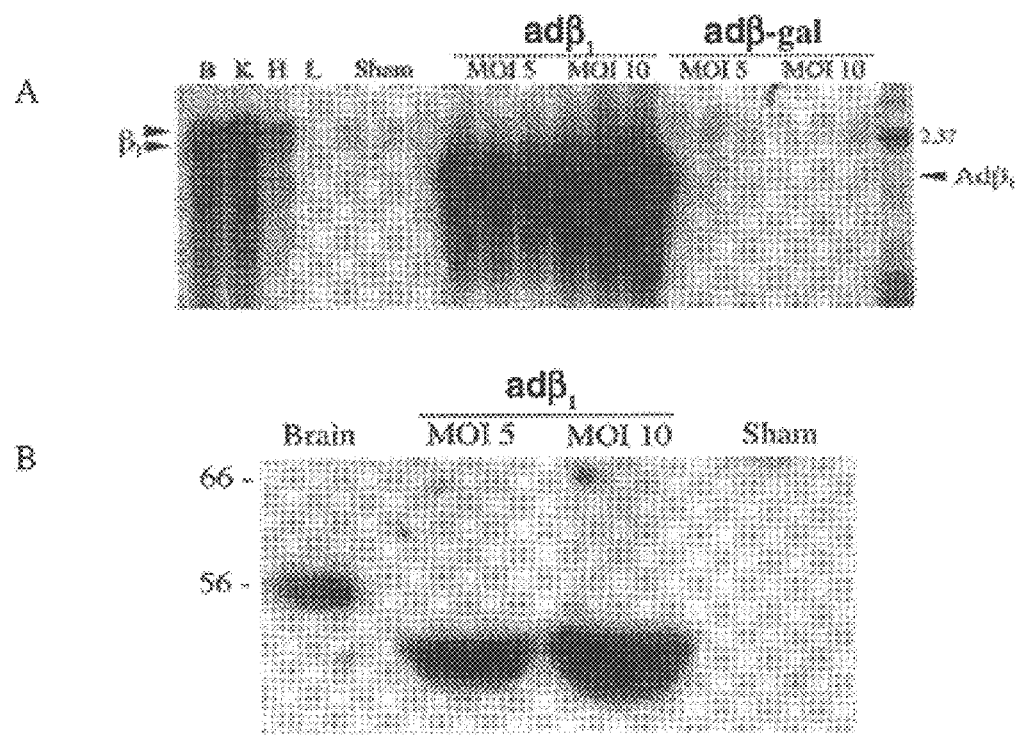
FIG. 2 shows northern blot analysis using a radiolabeled cDNA probe that corresponds to the rat $\beta_1$ Na,K-ATPase subunit gene (panel A); Panel B shows a western blot of whole lung tissue using a polyclonal anti-dog $\beta_1$ Na,K-ATPase antibody.

This invention provides therapeutic methods for the treatment in vivo of pulmonary edema in animals and humans, and compositions to effect the methods. The methods involve introducing recombinant genes, in particular DNA nucleotide sequences encoding Na,K-ATPase, into alveolar epithelial cells in viva. These cells transcribe and translate the recombinant genes, thereby increasing expression of a key transmembrane transport molecule and enhancing the lung's capacity to clear liquid from the alveolar airspace.

The methods of this invention involve the use of recombinant human adenoviral vectors for mediating the introduction of genes into alveolar epithelial cells. The recombinant adenoviral vectors of this invention are reported to produce superior results to other non-viral vectors (e.g. cationic lipids) in the transfer of genes into epithelial cells (Brody and Crystal, 1994). In particular, the methods of this invention involve the use of recombinant adenoviral vectors that mediate the transfer of Na,K-ATPase genes into alveolar and bronchial epithelial cells.

The vectors of the present invention employ expression control sequences consisting of viral derived promoter elements linked to cDNA molecules that express the $\alpha_1$, $\alpha_2$, and/or $\beta_1$ Na,K-ATPase subunit proteins. These proteins have been shown to be capable of generating the transepithelial osmotic gradient responsible for the movement of water across epithelial membranes. The transgenic proteins (Na,K-ATPase) produced by these vectors are transmembrane transport molecules that have been shown to be responsible for the active solute transport necessary to effect alveolar edema clearance. Extensive testing of Na,K-ATPase expressing adenoviruses showed that human lung epithelial cells in culture (A549) and cynomolgous monkeys require overexpression of the $\alpha_1$ or $\beta_1$ subunits, whereas rat alveolar epithelial cells and lungs require overexpression of the a subunit to increase Na,K-ATPase activity. Thus, the rate limiting subunit varies between cell types and species, and augmentation of Na,K-ATPase function requires overexpression of one, rate-limiting subunit.

That overexpressing nucleotide sequences encoding Na,K-ATPase subunit proteins resulted in increased edema clearance, was unexpected because Na,K-ATPase subunit proteins are already present in lung cells and are considered by some to be "housekeeping" genes that do not respond to acute stimuli (Suzuki-Yagawa et al., 1992). The transepithelial movement of $Na^+$ is dependent on the function of transport molecules on both the apical and basal cell membranes. The apical $Na^+$ channel is a passive conduit for the entry of $Na^+$. It is a tightly regulated channel that opens and closes in response to phosphorylation and dephosphorylation by membrane bound heterotrimetric G-proteins. It is considered by some to be the rate-limiting regulatory element in controlling vectorial $Na^+$ transport.

A new generation, high-capacity, helper-virus dependent adenoviral vector system of the present invention was developed to diminish adenoviral-induced host responses seen with earlier generation adenoviruses. These inflammatory responses have been attributed to the expression of adenoviral proteins in infected cells leading to a cytotoxic T cell response and clearance of infected cells (von Ginkel et al., 1997). The elimination of all adenoviral protein coding genes is expected to significantly abrogate this inflammatory response limiting host-mediated removal of adenovirus infected cells leading to more prolonged transgene expression than previously observed with first and second generation adenoviral vectors (Morsy et al., 1998; Schiedner et al., 1998; ). The helper-virus and cells (293Cre4) necessary to produce these helper-virus dependent vectors have been obtained from Merck by material transfer agreement. The DNA vectors (helper-virus plasmids) containing Na,K-ATPase cDNA's and promoter elements have been constructed by the inventor using human intronic DNA and fragments of wild-type human adenovirus type 5. These pieces are necessary for the construction of Na,K-ATPase expressing helper-virus dependent adenoviruses.

The high-capacity, helper-virus dependent vectors preferred for the present invention encode no adenoviral protein encoding DNA sequences (Mitani et al., 1995; Parks et al., 1996, 1997). Thus, host responses due to "leaky" adenoviral protein expression are unlikely to occur. This has been confirmed in recent publications that used similar vectors to overexpress $\alpha_1$ antitrypsin and leptin genes in mice (Morse et al., 1998; Schiedner et al., 1998). As opposed to mice given first generation adenoviruses, the livers of mice given high-capacity, helper-virus dependent adenoviruses were histologically "indistinguishable from (uninfected) control" and no elevation of hepatocellular enzyme levels were observed. This report indicated that a small quantity of helper adenovirus was concomitantly administered that did not induce a significant host response. It was also reported that diminution of inflammation attenuates the loss of adenoviral transduced cells extending the duration of transgene expression (Morsy et al., 1998; Schiedner et al., 1998)

Recent data indicates that adenoviral receptors are located on the basolateral aspect of bronchial epithelial cells limiting gene transfer to airway cells (Fasbender et al., 1998; Zabner et al., 1997). These receptors are likely expressed on the apical surface of alveolar epithelial cells. Thus adenoviral vectors are uniquely suited for a goal of alveolar (as opposed to airway) gene transfer. Other pulmonary gene transfer strategies, while efficient, do not at this time provide the combination of high gene transfer efficiency, ease of production, and relative specificity for the alveolar epithelium. Due to this unique combination of attributes, recombinant adenoviruses are preferred vectors for gene therapy for pulmonary edema.

Suitable promoters for the practice of the invention include constitutive promoter elements that include the immediate-early promoter from human cytomegalovirus. This viral promoter element is linked to expression control sequences that include the cDNAs for human, and other species, $\alpha_1$, $\alpha_2$, and/or $\beta_1$ Na,K-ATPase subunit genes. Additional regulatory sequences include the human SV40 t intron or human growth hormone polyadenylation signals and other transcriptional control signals such as splice donor-acceptor sites.

The invention described herein employs the use of helper-virus dependent adenoviral vectors that are devoid of all wild-type protein encoding adenoviral genes. These vectors are produced by cloning of an expression cassette that includes a constitutive or inducible promoter that is linked to an Na,K-ATPase cDNA followed by a polyadenylation sequence (e.g. SV40 t intron). This expression cassette is then inserted into a shuttle vector that contains the human adenovirus type 5 left and right inverted terminal repeats (ITR). Adjacent to the 3' end of the left ITR is the packaging signal from human adenovirus type 5. In between the ITRs is 10–12 kb of intronic DNA from the human hypoxanthine guanine phosphoribosyl transferase (hGPRT) gene obtained from the American Tissue Type Collection (Stout, et al., 1985, Ansorge, et al. 1990). Expression cassettes containing full-length Na,K-ATPase cDNAs are inserted within the human intronic DNA of the shuttle vector. When excised from its backbone by restriction endonuclease digestion, the 5' end of the shuttle vector contains an adenoviral wild-type inverted terminal repeat and an adenoviral packaging signal. The 3' end of this vector consists of an adenoviral wild-type inverted terminal repeat. The Na,K-ATPase subunit gene containing shuttle vectors (pHV10$\alpha_1$, pHV10$\alpha_2$, pHV12$\beta_1$) are co-transfected into HEK293cre4 cells with a recombinant helper adenovirus, adLC8cluc (Parks, et al., 1996). The adenovirus contains 2 loxP sites that flank a packaging signal. The remainder of adLC8cluc is similar to previously described (Parks et al., 1996) first generation Ela deleted recombinant adenoviral vectors (Factor et al., 1998 a and b). When transfected into cells that express cre recombinase (HEK293cre4, Graham, 1996) the packaging signal is effectively excised making it impossible for newly synthesized adLC8cluc to be packaged into adenoviral capsids. The remainder of the adLC8cluc genome contains the protein encoding adenoviral genes necessary to allow rescue of DNA sequences from the Na,K-ATPase subunit gene containing shuttle vectors, pHV10$\alpha_1$, pHV10$\alpha_2$, pHV12$\beta_1$ into the helper-virus dependent adenoviral vectors. The adenovectors thus produced are hv$\alpha_1$, hv$\alpha_2$, and hv$\beta_1$. These helper-virus dependent adenoviruses are propagated by infecting confluent 15 cm tissue culture plates of HEK293 cells with 3 pfu/cell. Following development of cytopathologic effect (CPE) the cells are harvested, concentrated and thermally disrupted via 6 cycles of freezing and thawing. The resultant cell lysate is cleared of cellular debris by high-speed centrifugation prior to purification through serial CsCl density gradient ultra-centrifugations. The resultant virus is dialyzed against 10 mM Tris HCl pH 7.4/1 mM MgCl/10% glycerol to remove CsCl prior to storage in 10% glycerol at −70° C. (McGrory at al., 1988, Factor, et al., 1998, Factor, et al., 1998). Helper-virus dependent adenovectors are titered based on optical density. The presence of the expected cDNAs is confirmed by PCR. The presence of adLC8cluc is assayed by plaque production counts following infection of HEK293 cells grown under agarose and by measurement of luminescence in cell lysates in a luminometer. Wild-type adenovirus is assayed by plaque production counts in A549 cells and by PCR for Ela DNA sequences.

There are many forms of ATPases, so selecting a suitable one was part of the criteria for success of the invention. Selection of regulatory elements was also important. Preliminary studies using first-generation replication deficient adenoviruses showed that endogenous regulatory elements were adversely affecting transgenic Na,K-ATPase subunit lifespan. This observation led to subsequent designs that employed the use of cDNAs in which all 5' and 3' regulatory elements were eliminated. Similarly, size constraints of what could be successfully transferred by the vector required the constriction of several $\alpha_1$ and $\alpha_2$ containing shuttle vectors that eliminated all 5' untranslated sequences and progressively reduced the amount of 3' untranslated sequences until a vector capable of homologous recombination was produced.

Vectorial Na$^+$ movement across tight epithelial is regulated, in part, by the apical Na$^+$ channel. This well studied polymeric transport molecule is tightly controlled and is postulated to be the regulator of the vectorial Na$^+$ movement necessary for the generation of the transepithelial osmotic gradients that effect water movement against osmotic or hydrostatic pressure gradients. Thus, it was unexpected that overexpression of individual Na,K-ATPase subunit genes in the present invention resulted in increased Na,K-ATPase function and edema clearance following adenoviral-mediated gene transfer without concomitant increases in apical Na$^+$ channel expression.

Delivery strategies capable of widespread delivery of adenoviral vectors of the present infection to the alveolar airspace include the use of a functional surfactant based vehicle and new methodologies for endotracheal instillation of adenovirus that include end-expiratory thoracic compression to drive end-expiratory lung volume toward residual volume and cause supra-physiologic inspiration to cause widespread distribution of vehicle and virus (Katkin et al., 1997, Factor, et al., 1998 a and b). These methods include safe endotracheal intubation and the use of a thoracic compression strategy aimed at driving end- expiratory lung volumes toward residual volume. These methods cause animals to take a deep/forceful inhalation that leads to widespread dissemination of adenovirus to all segments of the lung after thoracic compression is relinquished. This development is an important factor for human gene therapy using helper-virus dependent adenoviral vectors.

EXAMPLES

The following examples present embodiments of the methods and compositions of the present invention.

Example 1

Adenoviral-mediated Na,K-ATPase Gene Transfer to Rat and Human Alveolar Epithelial Cells in Vitro First generation human type 5 replication deficient adenoviruses arc deleted of sequences spanning all or part of the Ela, and Elb genes impairing the ability of these recombinant viruses to replicate outside of cells expressing these missing adenoviral DNA sequences. In the vector ad$\beta_1$, the early immediate promoter/enhancer element from human cytomegalovirus was used to drive transcription of a rat $\beta_1$ Na,K-ATPase gene with an SV40 t intron polyadenylation downstream from cDNA. Otherwise identical adenoviruses containing a rat$\alpha_1$ cDNA (ad$\alpha_1$), an E.coli lacZ gene (ad$\beta$-gal) or no cDNA (adNull) were also used in this and the following examples.

These viruses were produced using techniques known to those skilled in the art (Factor et al., 1998 a and b; McGrory, 1988) that include use of a plasmid that contains an expression cassette that includes the cDNA's encoding the Na,K-ATPase subunits flanked by portions of the left end of a human type adenovirus genome (shuttle vector) and a plasmid that contains an adenovirus genome that exceeds the packaging limits of the adenoviral capsid. These plasmids were co-transfected into human embryonic kidney cells (HEK294). Homologous recombination between these two plasmids produces an adenovirus genome of appropriate size to fit into the adenoviral capsid. Homologous recombination is detected by the presence of typical cytopathologic effects (CPE) in HEK293 cells. High titer recombinant adenoviruses were prepared by amplification in HEK293 cells using methods known to those of skill in the art. Virus was purified from cell lysates by serial cesium chloride ultra-centrifugation followed by desalting by dialysis against an isotonic, physiologic buffer. Virus thus produced was titered by enumeration of plaques produced following infection of sub-confluent HEK293 cells. Wild-type adenovirus contamination was assayed by plaque-production counts produced by serial dilution of adenovirus on A549 cells and via PCR for Ela DNA sequences. Presence of the desired cDNA was reconfirmed by PCR.

Figure 3:
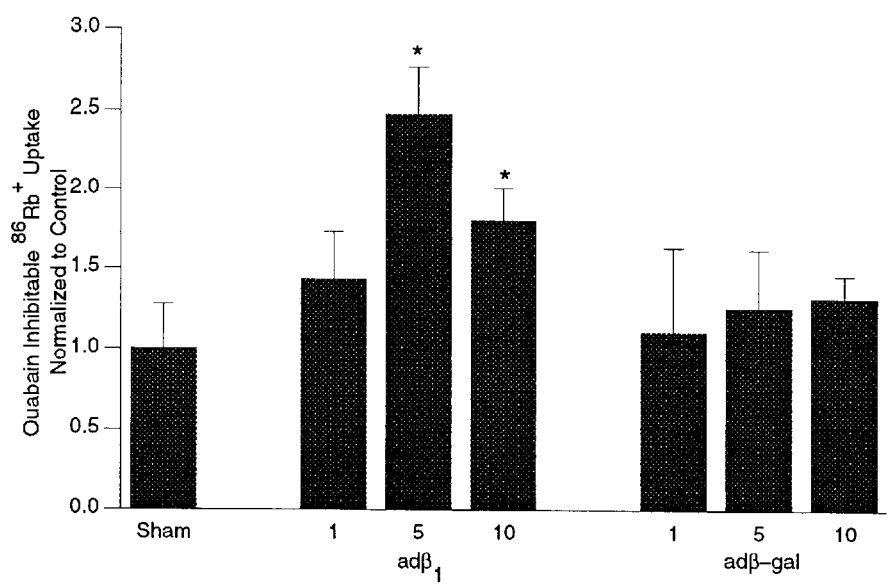
FIG. 3 shows Na,K-ATPase function following adenoviral-mediated Na,K-ATPase $\beta_1$ gene transfer to rat AT2 cells; Na,K-ATPase function was measured as ouabain sensitive uptake of the radiolabeled $K^+$ analog, $^{86}Rb^+$ vs. sham infected controls (*$p<0.001$, Student's t-test).

Alveolar type 2 epithelial (AT2) cells for this example were isolated from 200–230 gm male Sprague-Dawley rats using methods known to those of skill in the art that include elastase digestion and purification by panning on IgG coated plates (Dobbs et all., 1986; Ridge et al., 1997; Factor et al. 1998 b). To test for susceptibility to adenoviral gene transfer AT2 cells were plated on tissue culture treated plasticware and allowed to adhere for 24 hours prior to infection with ad$\beta$-gal. FIG. 1 shows rat AT2 cells infected with five or ten pfu/cell of ad$\beta$-gal and stained with X-gal 48 hours later. As compared to uninfected (sham) cells (left photomicrograph), adβ-gal produced β-galactosidase activity in >95% of cells when 10 pfu/cell was used (right photomicrograph). These photomicrographs indicate that recombinant adenoviruses are capable of highly efficient gene transfer into alveolar epithelial cells in vitro. To test for transgene activation, AT2 cells were infected with 5, or 10 pfu/cell of adβ$_1$ and compared to AT2 cells infected with similar titers of adβ-gal and to sham infected cells. Twenty-four hours after infection, transgene activation was measured via northern blot analysis (using a radiolabeled rat β$_1$ Na,K-ATPase cDNA probe) and western blotting (using an anti-dog β$_1$ antibody and horseradish peroxidase immunodetection method). AT2 cells infected with 5 or 10 pfu/cell of adβ$_1$ had marked increases in β$_1$ mRNA and protein (FIG. 3).

Similarly treated cells were used for measurement of Na,K-ATPase activity in AT2 cells infected with 1, 5 or 10 pfu/cell of adβ$_1$. These cells had up to a 250% increase in ouabain sensitive $^{86}$Rb$^+$ uptake confirming that adenoviral mediated gene transfer of a β$_1$ Na,K-ATPase subunit gene can augment Na,K-ATPase activity in alveolar epithelial cells in vitro. In other experiments AT2 cells were infected with adα$_1$ and no change in Na,K-ATPase activity was noted. FIG. 3 shows rat AT2 cells infected with a replication deficient adenovirus that expresses a rat β$_1$ subunit cDNA (adβ$_1$). Na,K-ATPase function shown as ouabain sensitive uptake of a K$^+$ analog ($^{86}$Rb$^+$) was increased by up to 250% in cells infected with five or ten pfu/cell. Infection with a virus that expresses E.coli lacZ (adβ-gal) did not change Na,K-ATPase function in these cells.

The adenoviral vectors disclosed in Example 1 were used to infect a human alveolar epithelial cell line (A549) to demonstrate functionality of the α$_1$ Na,K-ATPase expressing adenovirus vector, adα$_1$. These cells were derived from a human bronchoalveolar cell carcinoma and share some characteristics with AT2 cells. A549 have been extensively used to study alveolar epithelial function (Factor et al., 1998 b; Mason and Williams 1980; Smith, 1999).

A549 cells were plated on tissue culture treated plasticware and allowed to adhere for 24 hours prior to infection with adenovirus. Cells were infected with 1–200 pfu/cell of adα$_1$ or adβ$_1$ and were compared to cells infected with the same doses of an otherwise identical adenovirus that expresses an E.coli lacZ gene that produces the bacterial enzyme β-galactosidase (adβ-gal). Forty-eight hours after infection, transgene activation and protein production were measured using northern (using rat α$_1$ and β$_1$ Na,K-ATPase subunit specific radiolabeled cDNA probes) and western blot analysis (using a monoclonal anti-rat α$_1$ Na,K-ATPase subunit antibody, provided by Dr. K. Sweadner, University of Southern California). As compared to control cells and cells infected with adβ$_1$ or adβ-gal, adα$_1$ infected cells had significant levels of α$_1$ mRNA and protein. Na,K-ATPase function was assayed in these cells by measuring ouabain sensitive uptake of a K$^+$ analog ($^{86}$Rb$^+$). Adα$_1$ infected cells had Na,K-ATPase activity that was increased by up to 250% in A549 cells infected with >10 pfu/cell. Adβ$_1$ and adβ-gal did not affect Na,K-ATPase function in these in vitro experiments. (ad=adenovirus).

The rat α$_1$ subunit is extremely resistant to ouabain (IC$_{50}$=10$^{-3}$M) whereas the human α$_1$ isoform is sensitive to ouabain (IC$_{50}$=10$^{-5}$M). To demonstrate specificity of the effect of α$_1$ subunit over-expression, A549 cells were infected with 25 pfu/cell of adα$_1$ prior to measurement of Na,K-ATPase activity ($^{86}$Rb$^+$ uptake) in the presence of serial concentrations of ouabain (1×10$^{-11}$ to 1×10$^{-3}$ M). Inhibition curves were drawn using computer aided non-linear regression analysis. Results showed that adα$_1$ infected A549 cells had ouabain inhibition curves that were shifted to the right indicating decreased ouabain sensitivity. Data from adα$_1$ infected cells analyzed using non-linear regression analysis revealed a biphasic pattern that suggested the presence of two ouabain sensitivity patterns. Additional analysis revealed two IC$_{50}$'s that were different by more than two logs, confirming the presence of two α$_1$ Na,K-ATPase isoforms—ouabain-sensitive human and ouabain-resistant rat. Non-linear regression analysis of these curves allowed estimation of the relative contribution of each of these isoforms. This analysis indicated that the transgenic α$_1$ isoform contributed 60% of the total measured Na,K-ATPase activity, accounting for all of the observed increase in Na,K-ATPase activity above that seen in uninfected cells.

These results confirm the functionality of the adα$_1$ vector and suggest that, in contrast to the rat epithelial experiments, human alveolar epithelial cells require over-expression of the α$_1$ subunit to increase Na,K-ATPase activity.

Other studies were performed using an adenoviral vector that expresses a rat α$_2$ cDNA (adα$_2$). This virus was used to infect a human alveolar epithelial cell line (A549 cells) (Ridge et al., 1999). A549 cells infected with 100 pfu/cell had significant increases in Na,K-ATPase mRNA (measured via rtPCR using rat subunit specific oligonucleotide probes and normalized to GAPDH mRNA) and expression (measured via western blot analysis using a monoclonal anti-rat α$_2$ antibody). Na,K-ATPase activity, measured using ouabain sensitive $^{86}$Rb$^+$ uptake, was increased by >200 as compared to A549 cells infected with an otherwise identical adenovirus that expresses no cDNA (adNull).

Example 2

Adenoviral-mediated Gene Transfer to Rat Lungs in Vivo

To test if Na,K-ATPase subunit gene over-expression can affect the transepithelial osmotic gradient necessary to achieve pulmonary edema clearance, normal 280–300 gm male Sprague-Dawley rats were infected with the vectors disclosed in Example 1. Following dose-response experiments to determine the optimal dose required, rats were given 4×10$^9$ pfu/animal.

Figure 4:
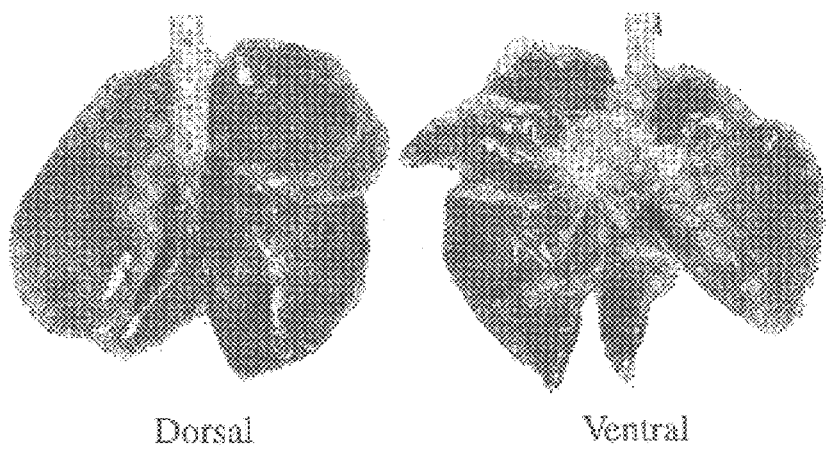
FIG. 4 shows dorsal and ventral views of X-gal staining of lungs of rats given $4\times10^9$ pfu of ad$\beta$-gal via tracheal instillation of adenovirus in a surfactant based vehicle.

250–300 gm male Sprague-Dawley rats were lightly sedated with pentobarbital prior to orotracheal intubation with a 14 g angiocatheter. Selected doses of adenovirus were suspended in 800 ml of a 50% surfactant/50% dialysis buffer mixture (Surfanta, Abbott Laboratories, Columbus, Ohio). Immediately prior to instillation of 200 ml of adenovirus solution, the thorax of each rat was circumferentially squeezed to approach residual lung volume and to stimulate the rat to exhale. Four instillations, at five minute intervals interspersed with 90° rotations of the animal, were used facilitate uniform delivery of the adenovirus. Immediately following endotracheal instillation of adenovirus- vehicle, compression of the rat was relinquished allowing the animal to take a deep, forceful inspiration that facilitated widespread, distal dispersion of adenoviral vector. To test the efficiency of this delivery scheme, four rats were given 4×10$^9$ pfu of an adenovirus that expresses a nuclear targeted E.coli lacZ gene and produces the bacterial enzyme β-galactosidase (adβ-gal). Seventy-two hours later, the lungs of these animals were harvested, fixed, and stained with X-gal (a substrate for β-galactosidase) for demonstration of β-galactosidase expression (Jaffe et al., 1992; Mastrangeli et al., 1993). FIG. 4 shows dorsal and ventral views of X-gal staining of lungs of rats given 4×10$^9$ pfu of adβ-gal via tracheal instillation of adenovirus in a surfactant based vehicle. Disseminated delivery and transgene expression is confirmed by presence of blue color throughout the lungs. X-gal staining of these lungs revealed widespread β-galactosidase expression in all lobes and segments of each of the adβ-gal lungs confirming that the delivery scheme used is capable of widespread viral delivery needed for studies of adenoviral-mediated Na,K-ATPase overexpression in vivo.

Figure 5:
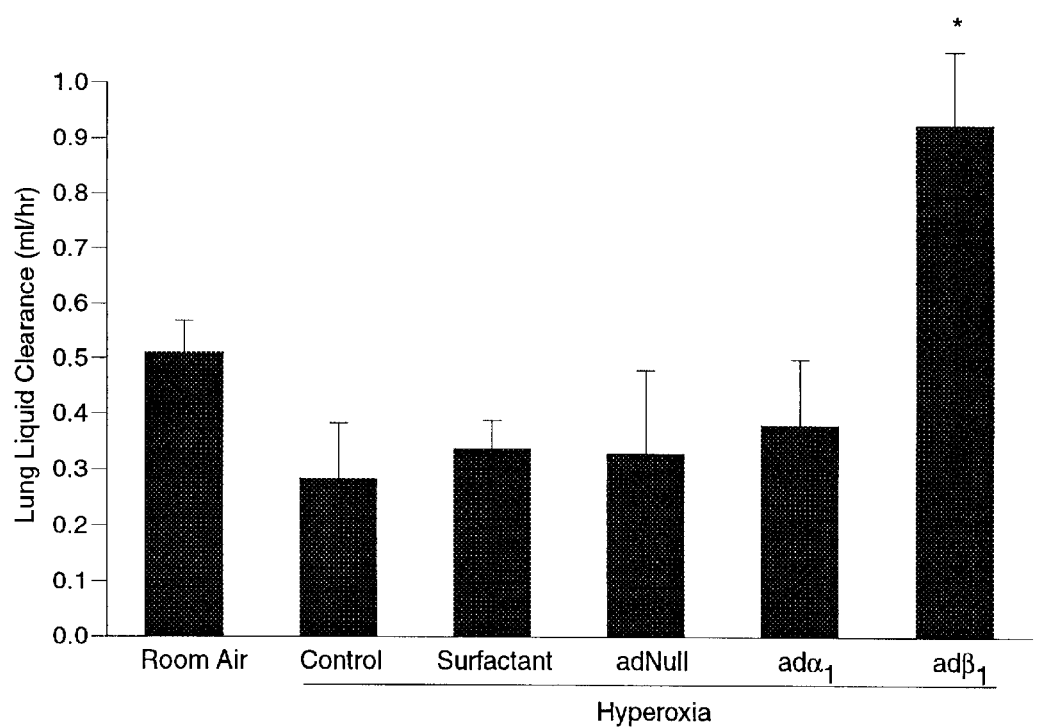
FIG. 5 shows lung liquid clearance in rats infected with $4\times10^9$ pfu of ad$\beta_1$, vs. sham infected controls (*$p<0.001$, Student's t-test)
Figure 6:
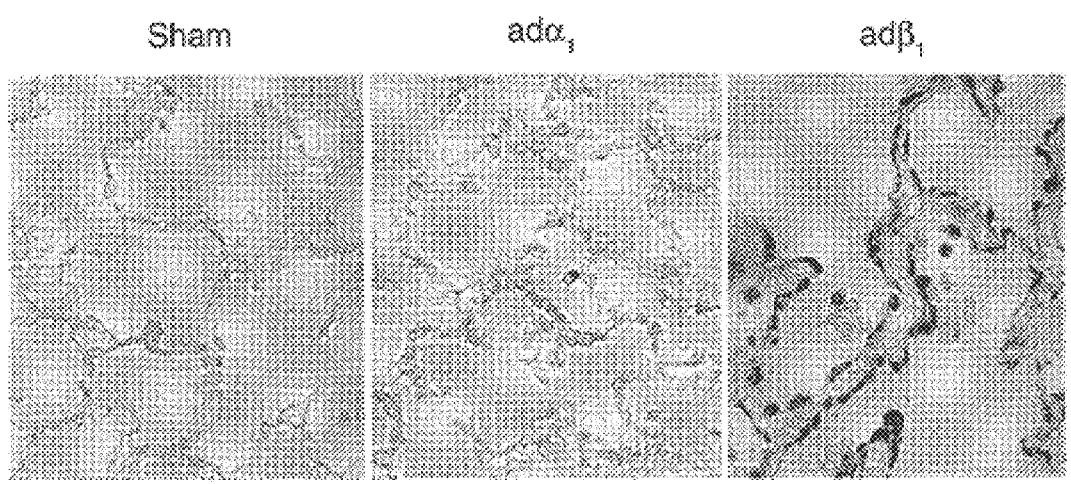
FIG. 6 shows photomicrographs (200x) of rat lungs either sham infected or infected with $4\times10^9$ pfu of ad$\alpha_1$ or ad$\beta_1$; lungs were immunostained with an anti-dog $\beta_1$Na,K-ATPase subunit antibody 7 days after infection.

To determine if Na,K-ATPase overexpression could affect alveolar edema clearance, rats were infected with 4×10$^9$ pfu of either adα$_1$ or adβ$_1$. Seven days after infection, alveolar edema clearance was measured using a well-established isolated lung preparation (Olivera et al., 1993, 1994; Barnard, 1997; Sznajder et al., 1995; Rutschman et al., 1993). As compared to controls, adβ$_1$ increased lung edema clearance by >100%. FIG. 5 shows lung liquid clearance in rats infected with 4×10$^9$ pfu of adα$_1$ is increased by >100% 7 days after infection. Adenoviral-mediated overexpression of the α$_1$ subunit did not change lung liquid clearance. Immunostaining of these lungs using an antidog β$_1$ Na,K-ATPase antibody demonstrated high-level β$_1$ protein expression only in the alveolar epithelium of rats given adβ$_1$. FIG. 6 shows photomicrographs (200×) of rat lungs either sham infected or infected with 4×10$^9$ pfu of adβ$_1$ or adβ$_1$. Lungs were immunostained with an anti-dog β$_1$ Na,K-ATPase subunit antibody 7 days after infection. As can be seen in the photo on the right, adβ$_1$ delivered via tracheal instillation produced marked increases in β$_1$ protein expression in all alveolar epithelial cells. This indicates that the use of a surfactant based adenoviral delivery system is capable of achieving overexpression of transgenic proteins in the alveolar epithelium. These results indicate that overexpression of a single Na,K-ATPase subunit, the β$_1$ Na,K-ATPase gene, can augment Na,K-ATPase expression and function in vivo.

Example 3

Tests of Adenoviral-mediated Na,K-ATPase Subunit Gene Overexpression in a Model of Acute Lung Injury (Acute Hyperoxia)

Rat lungs exposed to 100% O$_2$ for 64 hours (acute hyperoxia) have decreased Na,K-ATPase expression and diminished pulmonary edema clearance (Olivera et al., 1995). AT2 cells isolated from lungs treated with 100% O$_2$ have similar reductions in Na,K-ATPase expression and function. Thus, Na,K-ATPase expression parallels function in AT2 cells and rat lungs in this model of acute lung injury. Hyperoxic rats are acutely ill, have a high mortality (>50% at 72 hours), lose weight, and have significant pleural effusions (Crapo et al., 1980). Adenoviral-mediated overexpression of Na,K-ATPase subunit genes was used to determine if restoration of Na,K-ATPase expression and function in the alveolar epithelium could attenuate the reductions in pulmonary edema clearance seen following acute hyperoxic lung injury.

Figure 7:
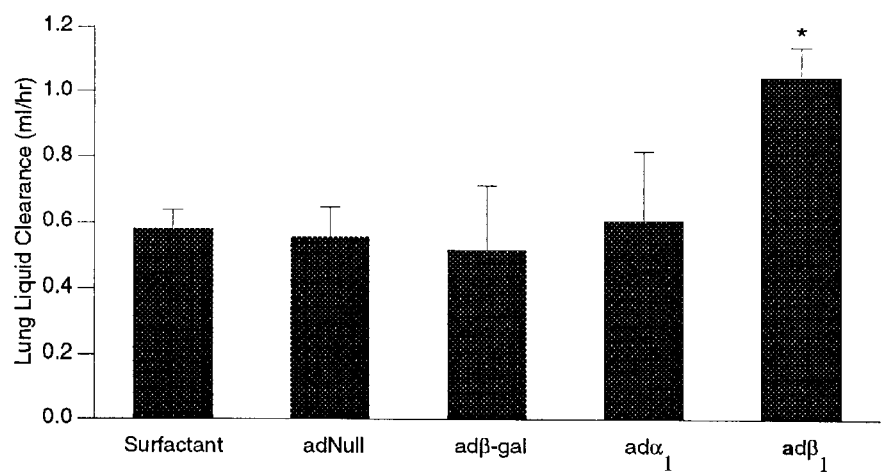
FIG. 7 shows lung liquid clearance after 64 hours of acute hyperoxia in rats infected with an adenovirus that overexpresses a Na,K-ATPase $\beta_1$ subunit gene (ad$\beta_1$) vs. untreated controls (*$p<0.002$, Student's t-test).

Male Sprague-Dawley rats were given 4×10$^9$ pfu of adα$_1$, adβ$_1$, or an otherwise identical adenovirus that contains no cDNA (adNull). These vectors were delivered as disclosed in Example 2 via tracheal instillation, to rats followed by recovery for seven days. They were then exposed to 100% normobaric oxygen for 64 hours prior to measurement of pulmonary edema clearance using a fluid-filled, isolated lung preparation. This method includes instillation of an isotonic, iso-osmotic solution that contains $^{22}$Na$^+$, $^3$H-mannitol and Evan's Blue Tagged albumin into the airspace. The vasculature is perfused at constant pressure with a similar isotonic solution that contains FITC-tagged albumin. The lungs are immersed in a bath consisting of an isotonic, buffered salt solution where temperature and pH are maintained within normal physiologic ranges. Changes in concentration of alveolar Evan's Blue Albumin over a sixty minute experimental period are used to calculate lung liquid clearance Movement of labeled substances between airspace and vascular compartments is used to measure alveolar and endothelial permeability (Factor, et al., 1998 b, Olivera et al., 1993, Olivera et al., 1994, Olivera et al., 1995, Barnard, et al., 1997, Sznajder, et al., 1995, Rutschman, et al., 1993). In subsequent studies, Na,K-ATPase overexpression was found to affect lung edema clearance and survival during acute hyperoxic lung injury. As compared to adα$_1$, adNull and uninfected controls, pulmonary edema clearance in infected hyperoxic rats was increased by >300%. FIG. 7 shows lung liquid clearance is increased by 300% after 64 hours of acute hyperoxia in rats infected with an adenovirus that overexpresses a Na,K-ATPase β$_1$ subunit gene (adβ$_1$). Lung liquid clearance in the adNull and adα$_1$ animals was not different than untreated hyperoxic controls. These results suggest that Na,K-ATPase overexpression restores alveolar epithelial function in the presence of an acute lung injury.

Figure 8:
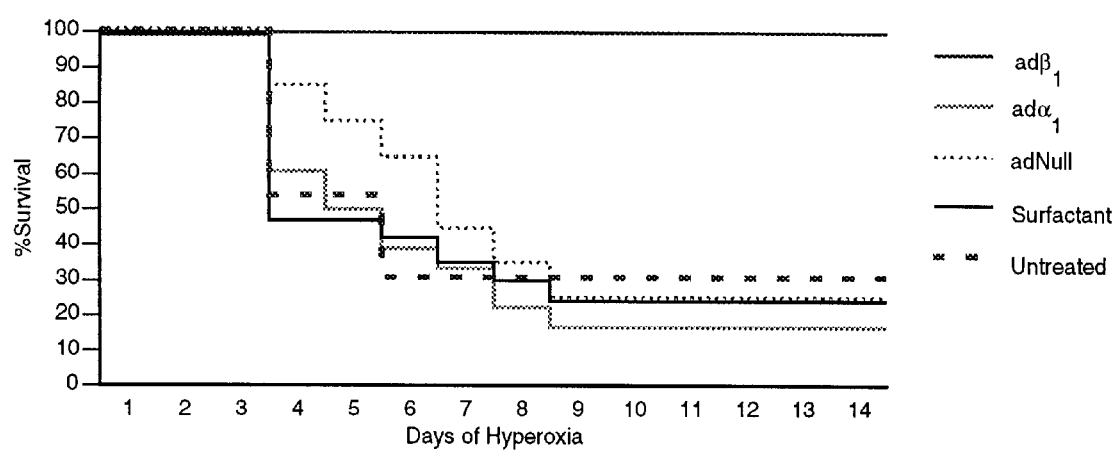
FIG. 8 shows survival of rats that were infected with $4\times10^9$ pfu of ad$\beta_1$ and allowed to recover for seven days prior to exposure to 100% normobaric $O_2$.

Survival studies were conducted in infected adβ$_1$ rats. Adult, male Sprague-Dawley rats were infected with 4×10$^9$ pfu of adβ$_1$ and allowed to recover for seven days prior to exposure to 100% normobaric O$_2$ for up to 14 days. All of the adβ$_1$ infected rats survived to the end of a 14-day experimental period (FIG. 8). Survival in the adα$_1$ and adNull groups was not different than surfactant or untreated controls (median survival≈4 days). Unlike the other groups, the adβ$_1$ animals appeared well, maintained their weight, and had no pleural effusions. Thus, overexpression of a Na,K-ATPase subunit gene improves lung edema clearance and survival during acute lung injury. These results also provide additional support for the importance of Na,K-ATPase function in the alveolar epithelium.

Example 4

Impact of Na,K-ATPase Overexpression in a Rat Model of Congestive Heart Failure (High-pressure Pulmonary Edema)

Elevation of left atrial pressures produces pulmonary edema in rats lungs. This model has been used previously for the study of pulmonary edema due to congestive heart failure. Measurement of pulmonary edema clearance, using a fluid-filled isolated lung preparation, in the presence of a left atrial pressure of 15 cmH$_2$O reveals reductions of clearance of >50%. Additionally, alveolar permeability for small solutes is slightly increased in these animals. Experiments using Na,K-ATPase and apical Na$^+$ channel inhibitors suggest that this reduction of active transport accounts, in part, for the reduced clearance seen in these animals.

Figure 9:
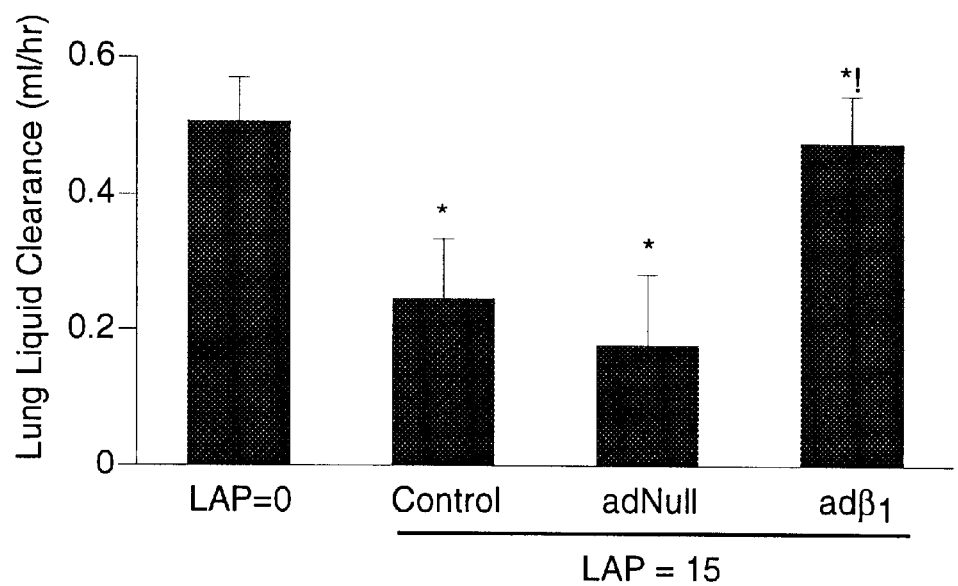
FIG. 9 shows lung liquid clearance in ad$\beta_1$ infected rats measured in the presence of elevated left atrial pressure vs. sham infected controls studied at a left atrial pressure of 15 cmH$_2$O (*$p<0.001$, Student's t-test).
Figure 10:
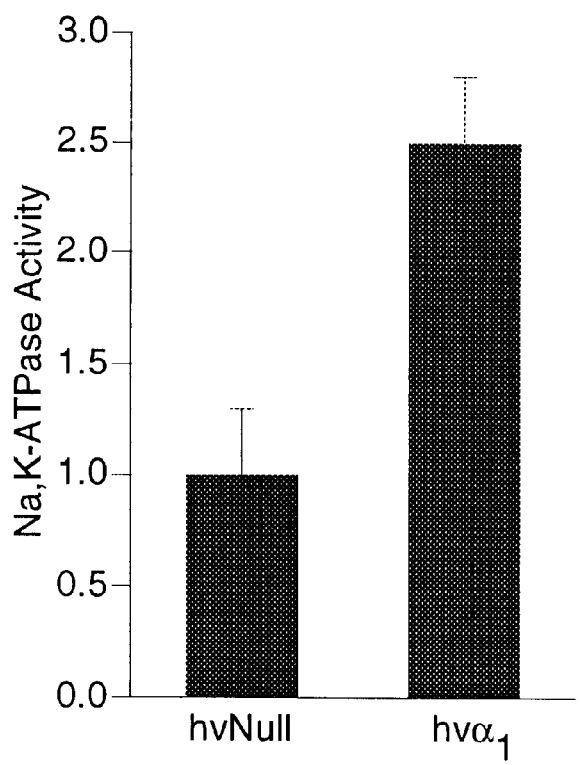
FIG. 10 shows Na,K-ATPase activity in human alveolar epithelial cells infected with a high-capacity adenoviral vector that encodes no adenoviral genes and includes a human Na,K-ATPase $\alpha_1$ subunit cDNA. Activity was measured as ouabain sensitive $^{86}Rb^+$ uptake. Data are presented normalized to hvNull infected controls vs. hvNull $\alpha_1$ infected controls (*$p<0.001$, Student's t-test)

Adult, male Sprague-Dawley rats were infected with 4×10$^9$ pfu of either adβ$_1$ or adNull as disclosed herein. Seven days following infection, their lungs were isolated and pulmonary edema clearance was measured in the presence of a left atrial (pulmonary venous) pressure of 15 cm H$_2$O. As compared to uninfected controls studied with a left atrial pressure of 0 cmH$_2$O, pulmonary edema clearance was reduced by 50% in adNull and uninfected controls. Edema clearance in the adβ$_1$ infected animals was increased by >100% as compared to the other animals studied at a left atrial pressure of 15 cmH$_2$O. FIG. 9 shows adenoviral-mediated overexpression of a Na,K-ATPase β$_1$, subunit gene returns lung edema clearance to normal seven days after endotracheal instillation of $4\times10^9$ pfu of adenovirus in rat lung in the presence of elevated left atrial pressures in a rat model of congestive heart failure. Thus, Na,K-ATPase subunit overexpression can maintain pulmonary edema clearance even in a model of congestive heart failure.

Example 5

Effects of Na,K-ATPase Overexpression in Primate Lungs

To determine if Na,K-ATPase overexpression could affect pulmonary edema clearance in primate lungs, adenovirus was administered to normal adult cynomolgous monkeys. Ten-millimeters of a 50% surfactant/50% saline vehicle containing $1\times10^{10}$ pfu of $ad\alpha_1$ or $ad\beta_1$ was delivered to the posterior basal segment of the right lower lung lobe of these monkeys. A similar volume of surfactant/saline vehicle without virus was delivered to the posterior basal segment of the left lower lobes of these same monkeys for use as an internal control. The monkeys were allowed to recover for three days prior to measurement of pulmonary edema clearance. Twenty-milliliters of an isotonic buffered salt solution containing Evan's blue-tagged albumin tracer solution was delivered to the posterior basal segments of the right and left lower lobes. Ten minutes later, 100 $\mu$l of tracer solution was aspirated for baseline determination of Evan's blue albumin concentration. Sixty-minutes later, a final aspirate was preformed. Changes in Evan's blue albumin concentration were used to calculate pulmonary edema clearance and the monkeys were allowed to recover.

As compared to the sham infected left lower lobes, pulmonary edema clearance increased by >6 fold following infection with $ad\alpha_1$. Unlike the rat experiments listed above, $ad\beta_1$ did not affect pulmonary edema clearance in this primate model. This data corroborates the studies listed above from human alveolar epithelial cells (A549) and suggests that the $\alpha_1$ subunit may be the rate limiting subunit in primate and perhaps human alveolar epithelium.

Example 6

Effects of Na,K-ATPase Subunit Overexpression Using a High-capacity, Replication-incompetent Adenovector to Transduce Human Lung Epithelial Cells in Vitro To test if a high-capacity helper-virus dependent adenovector can affect Na,K-ATPase function in vitro human lung epithelial cells (A549) were infected with a high-capacity, helper-virus dependent adenovirus that expresses a human Na,K-ATPase $\alpha_1$ cDNA (hv$\alpha_1$). Cells were infected with $8\times10^{10}$ viral particles of hv$\alpha_1$. Forty-eight hours post-infection Na,K-ATPase activity was ascertained by measuring ouabain sensitive $^{86}$Rb$^+$ uptake. As compared to cells infected with a similar virus that expresses no cDNA (hvNull), A549 cells infected with hv$\alpha_1$ had Na,K-ATPase activity that was increased by ≈250%. Western blot analysis of these cells showed significant increases in human Na,K-ATPase $\alpha_1$ subunit protein levels. These results are similar to that seen using first generation Na,K-ATPase expressing adenovectors in A549 cells. They also indicate that a high-capacity, helper-virus dependent adenovector can augment active Na$^+$ transport in vitro.

MATERIALS AND METHODS

Production of Helper-Virus Dependent Adenoviral Vectors

The invention described herein employs the use of helper-virus dependent adenoviral vectors that are devoid of all adenoviral protein encoding genes. These vectors are produced by transfection of a shuttle plasmid that contains Na K-ATPase subunit containing expression cassettes flanked by adenovirus ITR's and intronic DNA, into HEK293 cre4 cells, followed by infection with a replication deficient adenovirus that provides adenoviral protein sequences in trans position thereby allowing the generation of recombinant adenoviruses containing a genome comprised of DNA sequences from shuttle plasmid. The packing sequences of the helper-virus are flanked by loxP sites, when transfected into cells that expresses Cre recombinase (e.g. HEK293 cre4) the sequences between the loxP sites (i.e. the packaging signal) is excised rendering it unpackagable. This virus also contains a firefly lucifierase gene that allows ready detection of contamination by this adenovirus in subsequent steps of helper-virus dependent adenovirus production and use.

1. Production of pCM$\alpha_1$, pCMV$\alpha_2$ and pCMV$\beta_1$

Full-length cDNAs for human $\alpha_1$, $\alpha_2$ or $\beta_1$ Na,K-ATPase subunit genes were inserted into the polycloning site of pcDNA3 (Stratagene) or pCI (Invitrogen). These vectors include the human cytomegalovirus immediate-early promoter and either the human SV40 virus or growth hormone polyadenylation signals. Pme 1 endonuclease sites within these expression cassettes were eliminated using standard DNA cloning techniques. The shuttle plasmid vectors thus generated (designated pCMV$\alpha_1$, pCMV$\alpha_2$, and pCMV$\beta_1$) include an expression cassette containing a human cytomegalovirus immediate-early promoter element, a human Na,K-ATPase cDNA and a polyadenylation signal.

2. Production of pHV 1 and pHV12

A shuttle plasmid disclosed employs a eukaryotic expression phagemid backbone that includes an E. coli origin of replication and an ampicillin resistance gene (e.g., pBluescript SK$^+$ (Stratagene). Inserted into the polycloning site are the left ITR and packaging signal (corresponding to human adenovirus type 5 map units 0–1.2) and the right ITR (corresponding to map units 99.6–100). These fragments were produced via PCR using a first generation replication incombetent adenovirus as template. In between these elements is 10.3 or 12 kb (pHV10 and pHV12 respectively) of intronic DNA from the human HGPRT gene. The 10.3 kb fragment used to produce these plasmids was obtained by EcoRI digestion of the human hGPRT gene. The 12 kb fragment was obtained by inserting a 1.7 kb BgIII fragment of the human HGPRT gene into the BgIII site within the 10 kb EcoRI fragment gene were. The Na,K-ATPase containing expression cassettes from pCMV$\alpha_1$, pCMV$\alpha_2$, and pCMV$\beta_1$ are excised from their backbones by restriction endonuclease digestion and inserted (in sense or antisense orientation) within the intronic DNA to produced the shuttle vectors, pHV10$\alpha_1$ pHV10$\alpha_2$ and pHV12$\beta_1$ using standard DNA cloning methods.

3. Production of hv$\alpha_1$, hv$\alpha_2$, and hv$\beta_1$

The 14.6 kb, 14.8 kb, and 15.0 kb helper-virus dependent vector portions of pHV10$\alpha_1$ pHV10$\alpha_2$ and pHV12$_1$, respectively, are excised from their backbones via restriction endonuclease digestion with Pme1 and separated via agarose gel electrophoresis using low melting temperature agarose. Fragments are removed from the gel using a commercially available system (Wizard Preps, Promega, Madison, Wis.). These fragments are then transfected, using a lipid based methodology per manufacturers directions (Lipofectin, Gibco-BRL, Bethesda, Md.)) into HEK293 cre4 cells. Complete cell media is aspirated and changed to defined medium without antibiotic or antimyotic agents prior to lipofection. 2 hours later complete medium is added. Sub-confluent lawns (75–80% confluent) of HEK293 cre4 cells grown in 15 cm tissue culture treated plastic dishes are used. HEK293 cre4 cells are stable transformants that express both adenovirus E1a and cre recombinase genes (Parks et al., 1996). Approximately 18–24 hours following transfection these cells are infected with 1 pfu/cell of a packaging incompetent, E1a adenovirus, adLC8cluc. The packaging sequence of adLC8cluc is flanked by IoxP sites. When expressed in cre expressing cells DNA sequences in between the IoxP sites are excised. The removal of packaging sequences from adLC8cluc renders it unable to be inserted into the adenoviral capsid (e.g. unpackagable). The remainder of the adLC8cluc genome provides adenoviral protein genes in trans that produce adenoviral capsids into which the helper-virus dependent, packaging competent DNA from pHV10$\alpha_1$ pHV10$\alpha_2$, and pHV12$\beta_1$ can be inserted. The size of the DNA fragments excised from shuttle vectors is below that expected to be capable of packaging (Parks and Graham, 1997). Spontaneous combination (concatamerization) of 2 helper-virus dependent vectors into a single genome that is between 75% and 105% of the wild-type adenoviral genome size occurs spontaneously in HEK293cre4 cells making the method effective for the production of helper-virus dependent adenoviral vectors that are devoid of wild-type adenoviral protein encoding sequences (Morsy, et al., 1998). pHV10$\alpha_1$ pHV10$\alpha_2$ and pHV12$\beta_1$ were carefully designed to result in the production of adenoviral genomes that do not exceed 30 kb following concatamerization. The masses of these vectors are substantially less than the genome of adLC8cluc. This allows efficient separation, via ultracentrifugation, of helper-dependent adenoviruses from unexpected contamination/carryover of adLC8cluc. The Na,K-ATPase (gene containing helper-virus dependent adenoviruses thus produced are hv$\alpha_1$, hv$\alpha_2$ and hv$\beta_1$.

4. Propagation of hv$\alpha_1$, hv$\alpha_2$ and hv$\beta_1$

Twenty-four hours after transfection and infection, HEK293 cre4 cells are harvested and thermally disrupted by 6 cycles of freezing at −70° C. and thawing at 37° C. The resultant crude viral lysate is cleared of cellular debris by low speed centrifugation (800×g×10 minutes at 4° C.), the resultant supernatant is used to infect 15 cm tissue culture treated dishes containing confluent lawns of HEK293 cre4 cells that are simultaneously infected with 3 pfu/cell of adLC8cluc. Cells are again harvested after 24 hours and thermally disrupted. This cycle is repeated 4–5 times. The cells are then lysed by 6 cycles of freezing at −70° C. and thawing at 37° C. The resultant lysate is cleared of cellular debris by centrifugation (800×g at 4° C. for 10 minutes). The resultant supernatant is layered on a CsCl gradient that is created by layering 2.5 ml of CsCl solution with a density of 1.25 g/ml on top of 2.5 ml of a CsCl solution with a density of 1.40 g/ml (both solutions made from 10 mM Tris-HCl (pH 7.4), 1 mN MgCL$_2$ and sterilized by autoclave prior to use). The gradient is centrifuged in a swinging bucket rotor (e.g. Beckman SW41ti) at 150,000×g (35,000 rpm) for 1 hour at 120° C. The exterior of the centrifuge tube is disinfected with isopropyl alcohol and the resultant band that is closest to the bottom of the centrifuge tube is aspirated (using a sterile (20 g) through the wall of the tube. This aspirate is then layered on top of 8 ml of a sterile CsCl solution with a density of 1.33 g/ml and centrifuged at 150,000×g (Beckman SW41ti, 35,000 rpm) at 20° C. for 18 hours. The resultant band is aspirated as described above. (Factor, et al., 1998 a and b) CsCl is removed by dialysis at 4° C. against 1l of sterile phosphate buffered saline containing 10% glycerol for 4 hours with constant stirring, the dialysate is changed hourly. Helper-virus dependent vector titer is quantified by optical density readings at 260 nm (1OD=$10^{12}$ viral particles) and via immunocytochemistry of rat alveolar type 2 alveolar epithelial cells using Na,K-ATPase subunit specific antibodies (Upstate Biotechnology, Waltham, Mass.) following infection with serial concentrations of hv$\alpha_1$, hv$\alpha_2$ or hv$\beta_1$. The number of cells showing increased Na,K-ATPase subunit expression is enumerated to determine the number of infectious helper-virus dependent particles. The presence of adLC8cluc is assayed via plaque production counts following infection of HEK293 cells and by measurement of luminescence in cell lysates using a luminometer. The presence of wild-type adenovirus is assayed by measurement of plaque production counts following infection of human A549 cells and via PCR using E1a specific oligonucleotide primers.

PUBLICATIONS CITED

Ansorge, W., Caskey,C. T., Erfle, H. Zimmermann,J., Schwager, C., Stegemann, J., Civitello, A., Rice, P., Voss, H. and Edwards, A., *Genomics* 6, 593–608 (1990).

Barnard, M. L. et al. *Am. J. Resp. Crit. Care Med.* 156, 709–714 (1997).

Brody, S. L., Crystal, R. G. *Ann. N.Y. Acad. Sci,* 716, 90–101 (1994).

Crapo, J. D., Barry, B. E., Foscue, H. A., Shelburne, *J. Am. Rev. Respir. Dis.* 122, 123–143 (1980).

Dobbs, L. G., Gonzalez, R., Williams, M. C. *Am. Rev. Respir. Dis.* 134, 141–145 (1986).

Effors, R. M., Mason, G. R., Hukkanen, J., Silverman, P., *J. Appl. Physiol* 66, 906–919 (1989).

Factor, P. et al. *Am. J. Respir. Cell Mol. Biol* 18, 741–9 (1998).

Factor, P. et al. *J. Clin. Inves.* 102, 1421–1430 (1998).

Factor, P., Dumasius, V., Saldias, F., Sznajder, J. I. *Chest,* 116:S24–25 (1999).

Fasbender, A. et al. *J. Clin. Invest.* 102, 184–93 (1998).

Goodman, B. E., Fleishner, R. S., Crandall, E. D., *Am. J. Physiol.* 245, C78–C83 (1983).

Hall, J. B., Wood, L. D. H. in *Current Therapy in Respiratory Medicine,* R. Cherniack, Ed. (B. C. Dekker, Toronto, Canada, (1986) pp. 222–227.

Jaffe, H. A. et al. *Nat. Genet.* 1, 372–378 (1992).

Katkin, J., Husser, R., Langston, C., Welty, *S. Hum. Gene Ther.,* 8, 171–6 (1997).

Large State Peer Review Organization Consortium, *Arch Intern Med* 157, 1103–8 (1997).

Maniatis, T., Frisch, E., Sambrook, J. Eds., *Molecular cloning: A laboratory manual* (Cold Spring Harbor Laboratory, Cold Spring Harbor, N.Y., 1989).

Mason, R., Williams, M. *Biochim. Biophys. Acta.* 18, 36–50 (1980).

Mastrangeli, A. et al. *J. Clin. Invest* 91, 225–234 (1993).

Matthay, M., Wiener-Kronish, *J. Am. Rev. Respir. Dis.* 142, 1250–1257 (1990).

McGrory, W. J., Bautista, D. S., Graham, F. L. *Virology,* 163, 614–617 (1988).

Mitani, K., Graham, F. L., Caskey, C. T., Kochanek, S. *Proc. Natl. Acad. Sci.* 92, 3854–3858, (1995).

Morsy, M. A. et al. *Proc Natl. Acad Sci U.S.A.,* 95, 7866–71 (1998).

Olivera, W., Ridge, K., Wood, L. D. H., Sznajder, J. I., *Am. J. Physiol,* 266, L577–L584 (1994).

Olivera, W., Ridge, K., Wood, L. D. H. *J. Appl. Physiol* 75, 1581–1586 (1993).

Olivera, W. G., Ridge, K. M., Sznajder, J. I. *J. Resp. Crit. Care Med.* 152, 1229–34 (1995).

Parks, R. J., Graham, F. L. *J. Virol,* 71, 3293–8 (1997).

Parks, R. J. et al., *Proc Natl. Acad Sci U.S.A.,* 93, 13565–70 (1996).
Ridge, K. M. et al. *Am. J. Physiol.* 273, L246–55 (1997).
Ridge, K., Factor, P., Dumasius, V., Sznajder, J. I., *FASEB J.,* 13, A788, (1999).
Rosenfeld, M. A. et al. *Hum. Gene Ther.* 5, 331–342 (1994).
Rutschman, D. H., Olivera, W., Sznajder, J. I. *J. Appl. Physiol.* 75, 1574–1580 (1993).
Saldias, F. et al. *Am. J. Resp. Crit. Core Med.,* 159, A603 (1999).
Schiedner, G. et al., *Nat. Genet.* 18, 180–183 (1998).
Smith, B. *Am. Rev. Respir. Dis.* 115, 285–93 (1977).
Staub, N. C., *Prog Cardiovasc Dis* 23, 53–80 (1980).
Stout, J. T. and Caskey, C. T., *Annu. Rev. Genet.* 19, 127–148 (1985).
Suzuki-Yagawa, Y., Kawakami, K., Nagano, K. Mol *Cell Biol,* 12, 4046–55 (1992).
Sznajder, J. I., Olivera, W. G., Ridge, K. M., Rutschman, D. H. *Am. J. Resp. Crit. Care Med.* 151, 1519–25 (1995).
Sznajder, J. I., Zucker, A., Wood, L. D. H., Long, G. R., *Am. Rev. Respir. Dis.* 34, 222–228 (1986).
van Ginkel, F. W. et al., *J Immunol,* 159, 685–93 (1997).
Zabner, J., Freimuth, P., Puga, A., Fabrega, A., Welsh, M. J., *J. Clin Inves.* 100, 1144–9 (1997).

What is claimed is:

1. A method for increasing pulmonary edema clearance in a diseased mammalian lung, said method comprising:
    (a) obtaining a replication deficient adenovirus genetic vector comprising
        (i) an adenovirus genome that is deleted for all nucleotide sequences encoding adenovirus proteins; and
        (ii) a nucleotide sequence encoding a single Na,K-ATPase subunit; and
    (b) transferring the adenoviral genetic vector into epithelial cells of the lung via aerosol deposition or direct endotracheal instillation so as to express the nucleotide sequence encoding the single Na,K-ATPase subunit at levels that are an overexpression compared to levels in lung cells not having the genetic vector, whereby said pulmonary edema clearance of the mammalian lung is increased.

2. The method of claim 1, wherein the epithelial cells are alveolar.

3. The method of claim 1 wherein the subunit is in a rat and is $\alpha_1$.

4. The method of claim 1, wherein the encoded subunit is expressed in a human lung and is $\alpha_1$.

5. The method of claim 1, wherein the encoded subunit is expressed in a monkey lung and is $\beta_1$.

6. A pharmaceutical composition comprising a replication deficient adenoviral genetic vector comprising:
    (a) an adenovirus genome that is deleted for all nucleotide sequences encoding adenovirus proteins; and
    (b) a nucleotide sequence encoding a single Na,K-ATPase subunit.

7. The composition of claim 6, further comprising exogenous regulatory elements in said vector.

* * * * *